United States Patent [19]
Trachtenberg

[11] Patent Number: 6,143,556
[45] Date of Patent: Nov. 7, 2000

[54] ENZYME SYSTEMS FOR GAS PROCESSING

[76] Inventor: Michael C. Trachtenberg, 18543 Prince William, Houston, Tex. 77043

[21] Appl. No.: 08/984,666

[22] Filed: Dec. 3, 1997

Related U.S. Application Data

[63] Continuation of application No. 08/486,689, Jun. 7, 1995, abandoned.

[51] Int. Cl.[7] .................................................... C12M 3/00
[52] U.S. Cl. .................................... 435/289.1; 435/293.1; 435/297.1; 435/299.1
[58] Field of Search .............................. 435/289.1, 297.1, 435/299.1, 293.1

[56] References Cited

U.S. PATENT DOCUMENTS

| | | | |
|---|---|---|---|
| 4,073,686 | 2/1978 | Adams | 195/2 |
| 5,143,847 | 9/1992 | Kawase et al. | 435/288 |

*Primary Examiner*—David A. Redding
*Attorney, Agent, or Firm*—Martin L. McGregor

[57] ABSTRACT

The invention provides a process for gas separation wherein a selected gas in a mixed gas stream is contacted by an enzyme having an active site directly contacted by the mixed gas stream, and the selected gas is at least partially removed from the mixed gas stream. In one embodiment a selected gas in a gas phase is contacted by a solvated enzyme wherein the enzyme active site is in direct contact with the gas phase, and the selected gas is converted to a first product in a condensed phase by contact with the solvated enzyme. The invention also provides a bioreactor which comprises a vessel having at least one first wall enclosing an inlet zone, and at least one second wall enclosing a second phase zone, a portion of the second wall is permeable to at least one selected gas in the inlet zone, and retains the second phase in the second phase zone; a portion of the second wall also comprises a support surface with at least one enzyme fixed thereon, such that a mixed gas stream entering the inlet zone contacts enzyme which removes a selected gas from the mixed gas stream and passes the selected gas to the second phase zone. The invention also provides an alternative bioreactor which comprises buoyant beads coated with enzyme, floating on the surface of a condensed fluid phase, in contact with a gas phase such that the active site of the enzyme is in direct contact with the gas phase, and the beads are free to rotate in response to motion in either phase, and means for producing motion in at least one phase such that portions of the beads alternately contact the gas phase and the fluid phase, bringing a selected gas into the condensed fluid phase.

7 Claims, 6 Drawing Sheets

Bioreactor
Gas to Liquid to Gas Phase Transfer

Carbon Dioxide
Bioreactor
Embodiment

Gas to Liquid to Gas Phase Transfer

Urea
Bioreactor

Gas to Liquid Phase Transfer

Peroxide Bioreactor

Gas to Gas Phase Transfer

Fig. 5A. Partially Coated Bead

Fig 5B. Fully Coated Bead

Enzyme Immobilized on Buoyant Beads

Gas to Liquid Phase Transfer

A Phase Rotating Immobilized Enzyme Carrier

Phase Rotating Immobilized Enzyme Carrier System

ENZYME SYSTEMS FOR GAS PROCESSING

RELATED APPLICATIONS

This application is a continuation of application Ser. No. 08/486,689, filed Jun. 7, 1995 now abandoned.

TECHNICAL FIELD

This invention relates to a process utilizing natural, modified or engineered enzymes as agents, alone or immobilized in conjunction with membranes or other techniques or cells or cell fragments for the extraction of one or more specific molecules from a mixture of molecules in a first gaseous phase and moving at least one specific molecule to a second phase. Preferably the mixture of molecules is in a first gas phase and a specific molecule type is transported to a second mobile fluid phase. The specific gases to be separated may be present in a gas mixture, or in solution of mixed gases. In a mixed gas solution in a liquid phase, the specific gases can be treated either in their dissolved or solvated molecular state or after they have been converted to an ionic or ionized state either by reaction with water, reaction with another solvent, or by other prior chemical reaction. The invention process may also be used to regenerate a specific gas from the second phase. The invention further relates to the extraction of gases, molecules or ions from a liquid solution, aqueous or non-aqueous, to concentrate or isolate specific materials alone or in chemical combination and in ionic or non-ionic form.

BACKGROUND OF THE INVENTION

Traditional means of isolating selected gases from a mixed stream involve physical, chemical reactions or a combination thereof, and inert semipermeable membranes. Among such processes are cryogenic, gas-liquid and gas-solid sorptive techniques (e.g. pressure swing adsorption, amine treatment, iron sponge, etc.), and immiscible liquid—liquid extraction (for recent summaries see Michaels A S: New vistas for membrane technology, *Chemtech.* 19:160–172, 1989; and Babcock R E, Spillman R W, Goodin C S & Cooley T E: Natural gas cleanup: A comparison of membrane and amine treatment processes. *Energy Prog.* 8(3):135–142, 1988.) Newer technologies focus on the use of inert semipermeable membranes but these do not offer a separation solution that is particularly unique over existing processes (Spillman R W: Economics of gas separation membranes. *Chem. Engr. Prog.* 85:41–62, 1989). Membrane systems have been said never to achieve complete separation (Spillman, id. 1989). Prior art physical or chemical means do not readily allow segregation among gases with similar physical or chemical properties or those in low concentrations. In general prior art does not effectively deal with extracting gases or gas equivalents from a dissolved or ionized state to regenerate a purified gas. The prior art generally treats gases already dissolved in water such as carbon dioxide or oxygen in Bonventura et al., U.S. Pat. Nos. 4,761,209 and 4,602,987 and carbon dioxide in Henley and Chang U.S. Pat. No. 3,910,780. No reference has been located in which the enzyme contacts a gas in a gas stream, separates the gas and in a subsequent step regenerates a purified gas.

Traditional gas separation means commonly exhibit one or more of the following problems: they are energy inefficient, commonly nonspecific, quite slow, require a relatively pure feedstock, depend on a significant pressure head, or use ecologically questionable or toxic compounds. The relatively pure feed stock requirement may result in a geographical restriction of available feed materials. The geographic availability may require shipment from distant locations such that transportation costs may be high, and even prohibitive for some uses. The preceding limitations present restrictions on the growth and application of gas extraction/purification systems. A gas separation or enrichment process that did not require highly concentrated feedstocks thus eliminating or reducing transportation requirements would be beneficial.

In contrast to the disadvantages enumerated above for traditional physical/chemical methods, biological catalysts (enzymes) present several advantages including enhanced efficiency, speed, and increased specificity. Enzymes also commonly distinguish optical isomers. Further, they can be used at moderate temperatures and pressures, enhancing safety.

Prior use of enzymes has focused very largely on the food processing industry, cleansing or detergent applications, or processing of sewerage. Industrial applications in the gas field have been limited. Prior application of enzymes to gas extraction are found in patents to Bonaventura et al, U.S. Pat. Nos. 4,761,209 and 4,602,987 and Henley and Chang U.S. Pat. No. 3,910,780. Bonaventura uses membranes impregnated with carbonic anhydrase to facilitate transport of $CO_2$ across a membrane into water in an underwater rebreathing apparatus. Henley and Chang make a similar use carbonic anhydrase. Both processes operate on dissolved carbon dioxide. Neither taught fixation of the enzyme with the active site exposed to the gaseous phase with sufficient hydration to maintain a reactive conformation. Neither taught modification of DNA coding for enzymes to build in specific structure for fixation or enhanced catalysis. Indeed Bonaventura took for granted that the crude coupling techniques disclosed would deactivate a large fraction of the active enzyme. The Bonaventura patents contain computations showing that only a small fraction (1%) of the carbonic anhydrase need retain its activity in the bonded membrane to provide adequate capacity to remove carbon dioxide from the proposed apparatus in the illustrative uses. Henley and Chang do not discuss activity losses nor provide any description of fixation techniques to enhance enzyme activity when in the active site is directly exposed to a nonaqueous environment.

Despite some significant advantages, a variety of major problems have limited the application of enzymes in industrial settings. These include short lifetime of either free or immobilized enzyme, fouling and biofouling, separation of the enzyme from the immobilization surface, limited availability of enzymes in sufficient quantity, and expense of manufacture.

These problems have resulted in relatively few efforts to use enzymes for manipulation of gases. Further, physical/chemical means are in place commercially; they are understood and represent established technology and significant investment.

Despite these historic considerations a number of recent developments now allow broad based enzymatic applications. First, the development of DNA libraries and the techniques needed to generate such libraries so that large amounts of enzyme can be made economically. Previously, and even today, many enzymes are derived by purification from a biological source. Second, development of techniques to generate membrane expression of enzymes and even direct secretion such that harvesting the enzymes is easier and economically feasible. Third, the development of new immobilization techniques which allow long lifetime and high efficiency.

SUMMARY OF THE INVENTION

The invention provides a process for gas separation wherein a selected gas in a mixed gas stream is contacted by an enzyme, and the selected gas is removed from the gas stream. The selected gas may also be recovered as a separated gas. In one embodiment the invention provides a process for gas treatment wherein a selected gas in a gas phase is contacted by a solvated enzyme wherein the enzyme active site is in direct contact with the gas phase, the selected gas is converted to a first product in a condensed phase by contact with the solvated enzyme. In a preferred embodiment the hydrated enzyme is partially covered with a hydrocarbon film. In another preferred embodiment the hydrocarbon film is a lipid layer, more preferably the lipid layer is a phospholipid and most preferably the phospholipid is a bilayer. In a preferred embodiment, the first product is further contacted with a second enzyme in the condensed phase and converted to a second product, which maybe the originally selected gas or a different material. In an alternative embodiment the invention provides a process for gas treatment wherein a selected gas in a gas phase is contacted by a solvated enzyme wherein the enzyme active site is in direct contact with the gas phase, the selected gas is converted to a first product in a condensed phase by contact with the solvated enzyme, the first product is further contacted with a second enzyme in the condensed phase and converted to a second product. In an alternative embodiment a simplified bioreactor is provided which comprises buoyant beads coated with enzyme, floating on the surface of a condensed fluid phase, in contact with a gas phase such that the active site of a portion of the enzyme coating is in direct contact with the gas phase, and the beads are free to rotate in response to motion in either phase, and means for producing motion in at least one phase such that portions of the beads alternately contact the gas phase and the fluid phase, bringing a selected gas into the condensed fluid phase. In a preferred embodiment the enzyme is immobilized on the bead surface. In an especially preferred embodiment the enzyme is carbonic anhydrase, and the condensed fluid phase is water.

The invention also provides novel apparatus for practicing the process for gas separations. The method couples use of selective enzymes and immobilization by several distinct means in conjunction with a variety of support structures or membranes to achieve gas enrichment, purification, separation and processing of gas mixtures. The process of the invention can be used in a selective or subtractive manner, and provides on location separation and purification, thereby avoiding transportation problems. The invention also encompasses advanced enzyme fixation methods resulting in higher enzyme activity than the crude cross linking techniques fixation of Bonaventura et al. The present invention is the first to provide enzyme immobilization with active site exposure directly to gas phase substrates.

The invention is a process to achieve vectorial movement and separation of one or more gas substrates admixed with several other gases, thus isolating a selected gas from a mixture. The invention may be used to detect and measure the gas, to subsequently purifying the selected gas, or to convert selected gases to new chemical entities.

In apparatus provided for practicing the invention, an appropriate enzyme or enzymes are present at the supply side to effect a change in state or chemistry of the selected gas and thereby generate a reaction product and reduce or prevent exit of the enzyme reaction product back to the gaseous supply side. Solubility and concentration factors favor movement of the enzyme reaction product into a second phase which also contacts the enzyme. The second phase may be a second gas stream, or a solvent or a solvent doped with ions or other chemical materials to facilitate retention of the enzyme reaction product. Further treatment of the second phase may recover the selected gas as a purified or concentrated stream, or further react the selected gas or gases to produce a desired chemical entity.

Accordingly, the several objects the invention are to provide a process wherein gas mixtures are effectively separated so that at least one species may be isolated and/or enriched. Another object is to extract a selected gas for independent use or to serve as a start material or substrate for another physical, chemical or biological operation. Another object is to process ionic equivalents of a gas, present in a solution, to extract the ionic gas equivalents in the form of a gas or to use the material as a substrate for another physical, chemical or biological operation. Another object of the present invention is to allow serial, parallel or sequential processing of gas mixtures for sequential isolation or enrichment of gases. Another object is to allow very large volumes of gas to be produced, not heretofore possible. Another object is to allow enrichment or removal from gas mixtures in which the object gas species is in low concentration. Another object is to allow location of the separation facility at or near to the site of final use to reduce or eliminate transportation. Another object of the invention is to allow appropriately sized production facilities to meet the needs of each user. Another object is to allow placement of gas generating facilities anywhere in the world, or in space.

Further objects of the present invention are to utilize a low purity gas source. Yet another object is to treat the effluent from any kind of smoke stack, stationary or mobile, to process gases including carbon dioxide, oxides of nitrogen, oxides of sulfur, hydrogen sulfide, methane, ozone, or chlorofluorocarbons. Carbon dioxide removal from gas streams is a particularly preferred objective for gas processing.

The invention also provides apparatus for practicing the processes of the invention selected embodiments of which are illustrated by the drawings. Those skilled in the art will recognize that many changes and substitutions may be made without departing from the spirit of the invention as described herein. The drawings and descriptions are provided for illustration and not for limitation. The invention is defined and limited by the claims set out below.

DETAILED DESCRIPTION OF THE INVENTION

Figure 1:
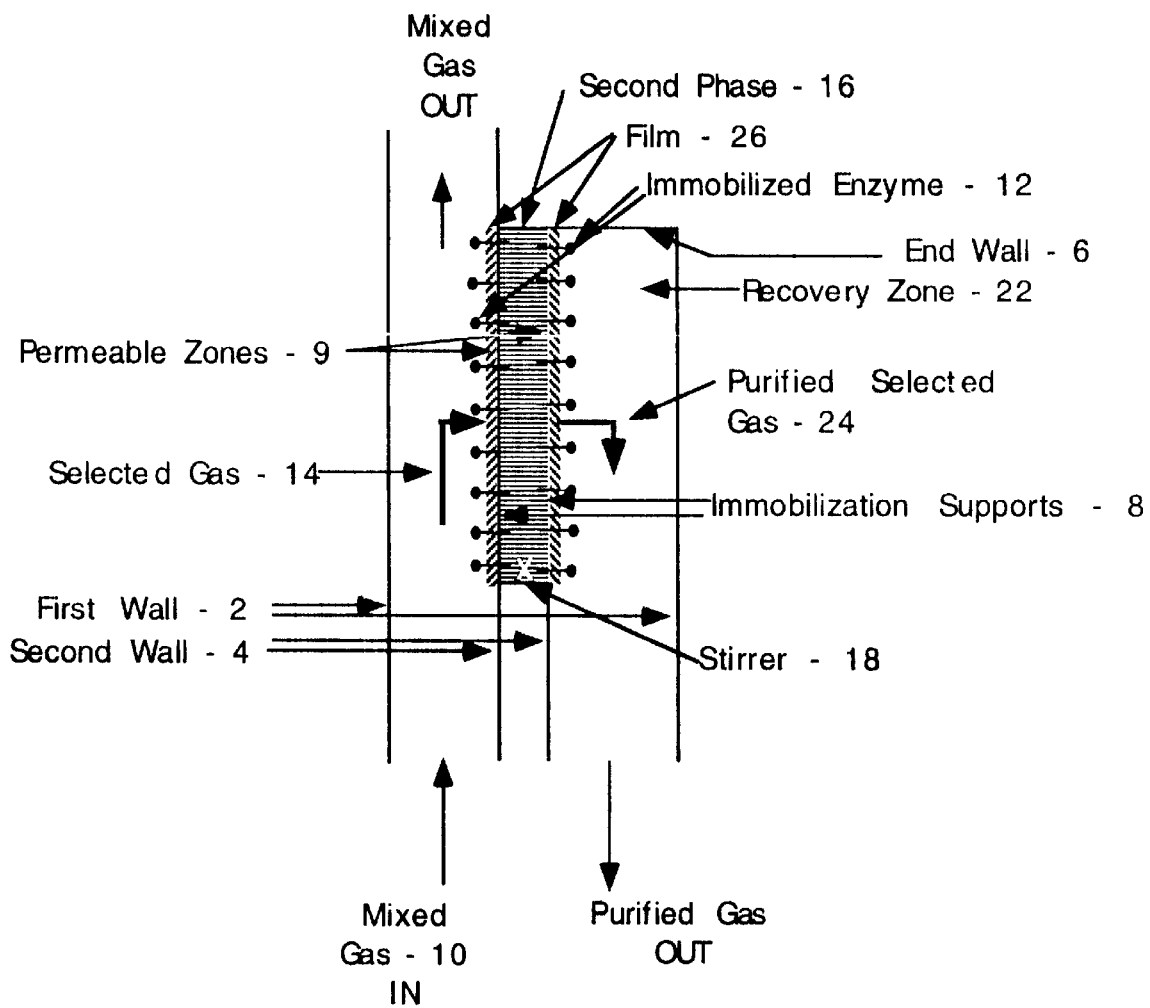
FIG. 1 illustrates a simplified bioreactor for separation of a selected gas.

FIG. 1 illustrates an apparatus for practicing the invention as a process for gas separation wherein a selected gas in a mixed gas stream is contacted by an enzyme, and the selected gas is removed from the gas stream. The apparatus allows the selected gas to be recovered as a separated gas.

The bioreactor comprises a vessel having at least one first wall 2 and at least one second wall 4, and an optional end wall 6 which closes a portion of the volume enclosed by first wall 2 and second wall 4. A portion 9 of second wall 4 is permeable to at least one selected gas and also comprises a support surface 8 for enzyme immobilization; a mixed gas stream 10, from a gas source not shown, enters a space between first wall 2 and second wall 4 wherein the mixed gas stream 10 contacts immobilized enzyme 12 fixed to support surface 8 which removes selected gas 14 from mixed gas stream 10; selected gas 14 interacts with immobilized enzyme 12 and is caused to enter second phase 16 which is in fluid contact with immobilization support 8 and immobilized enzyme 12 and confined with the volume enclosed by second wall 4 and optionally end wall 6; second phase 16 may be a low pressure carrier gas stream or vacuum line, or a liquid or gas permeable gel, alternatively second phase 16 may be stirred by optional stirrer 18 or circulated by an optional pump, not illustrated. An appropriate enzyme or enzymes are present at permeable portion 9 to effect a change of state or chemistry of selected gas 14 and thereby reduce of prevent exit of the selected gas 14 back to the supply side. The desired vectorial movement of selected gas 14 into phase 16 may be promoted by concentration effects, solvation, chemical conversion, ionization, or other means to favor movement of selected gas 14 or its enzyme reaction product 15 into second phase 16.

Figure 2:
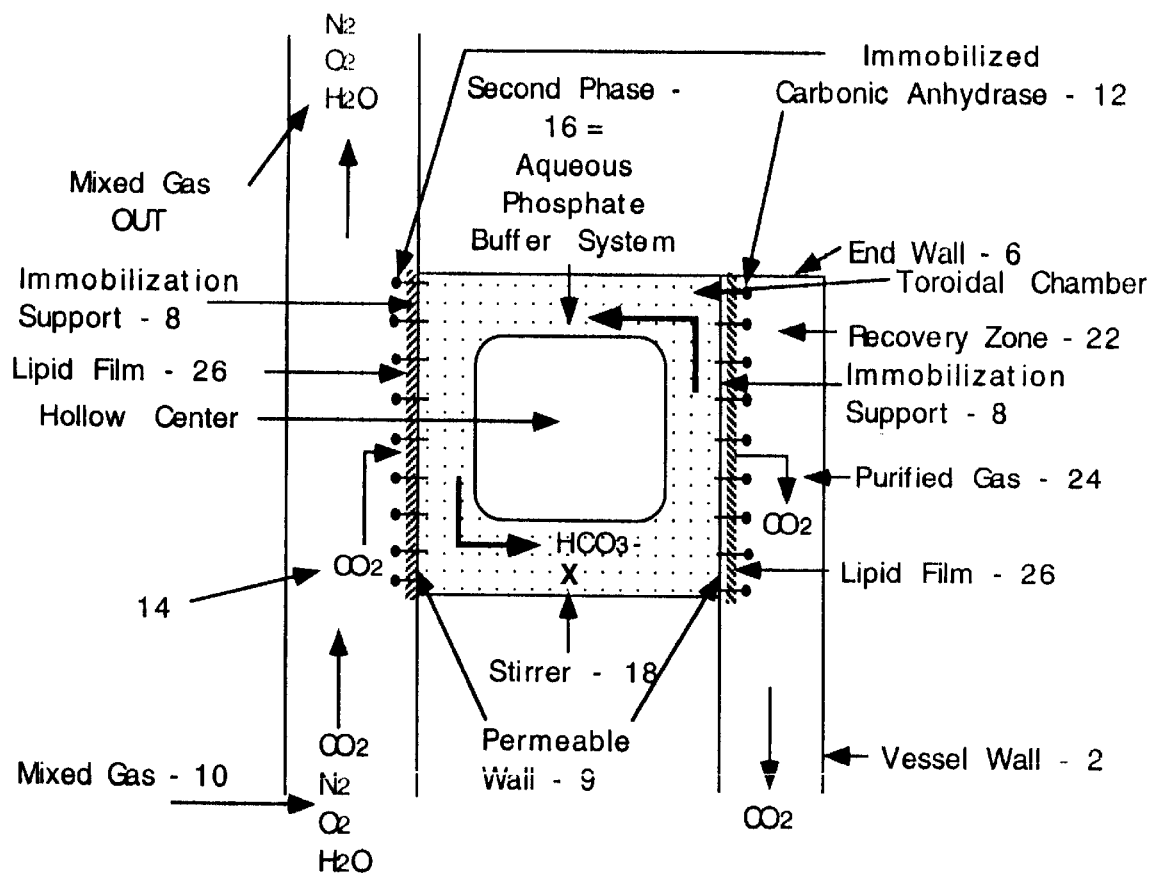
FIG. 2 shows a reactor set up for recovery of carbon dioxide from a flue gas stream.
Figure 3:
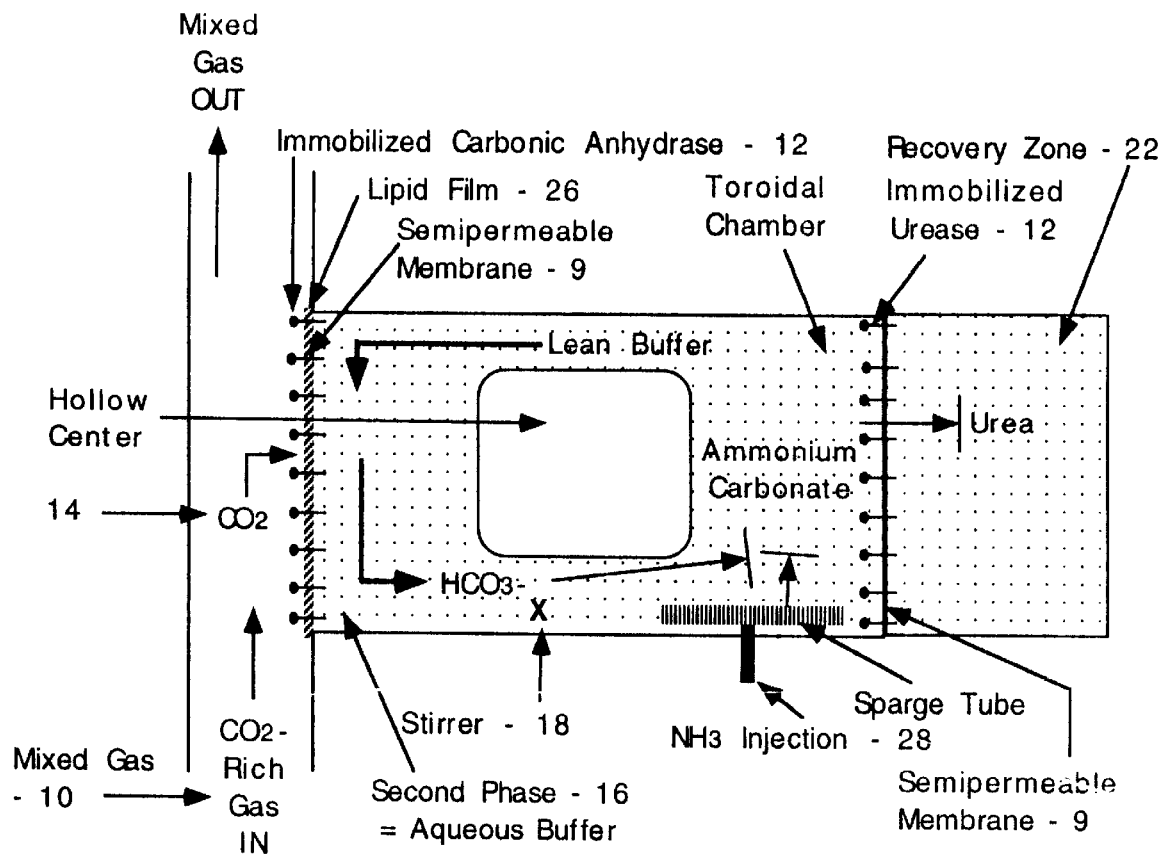
FIG. 3 shows a multienzyme reactor for production of urea.

If desired, second phase 16 may flow through the area enclosed by second walls 4 by use of a suitable port, not shown, and second phase 16 may also be recirculated through a recycling loop not shown. The selected gas 14 or its enzyme reaction product 15 may be used in second phase or may optionally be further processed. Additional support surface 8, permeable area 9 and immobilized enzyme may be provided in second wall 4 to connect second phase 16 to a recovery zone 22 enclosed by first wall 2, or second wall 4, or a combination thereof, and optionally end wall 6 and recovered as a further reacted product or as a concentrated gas by, for example, reverse reaction with the same immobilized enzyme to generate a recovered purified selected gas 14. A concentration gradient or other means will be used to favor vectorial movement of selected gas 14 or enzyme reaction product 15 from second phase 16 to recovery zone 22. Any of the means previously listed can be also be applied at this stage to provide movement into recovery zone 22. If desired, one or more different enzymes or other catalysts may be placed between second phase 16 and recovery zone 22 to further convert selected gas 14 to a new product. Additional stages may be added to further change or process selected gas 14 or its enzyme reaction product 15 as may be desired. FIG. 2 illustrates a reactor removing carbon dioxide from a mixed gas stream such as animal respiratory gases by contact with carbonic anhydrase, conversion of carbon dioxide to bicarbonate, and subsequently reconverting bicarbonate to carbon dioxide as a concentrated gas stream. FIG. 3 illustrates a multienzyme reactor system which converts carbon dioxide and ammonia to urea.

In a reactor of the type illustrated by FIG. 1, elements and areas maybe interchanged to provide many alternative structures as will be apparent to those skilled in the art. The mixed gas stream 10 may be pretreated to provide an optimal temperature or pressure, or to remove components that would lower the reactor's efficiency, or contribute components that may pass through the selection media to contaminate purified selected gas stream 24, or recovered product 25. Examples of pretreatment include mechanical screening by filters, chemical screening by adsorbents or absorbents, or scrubbing, and use of heat exchangers, waste heat recovery processing, compression, expansion and other gas processing steps known in the art.

Figure 5:
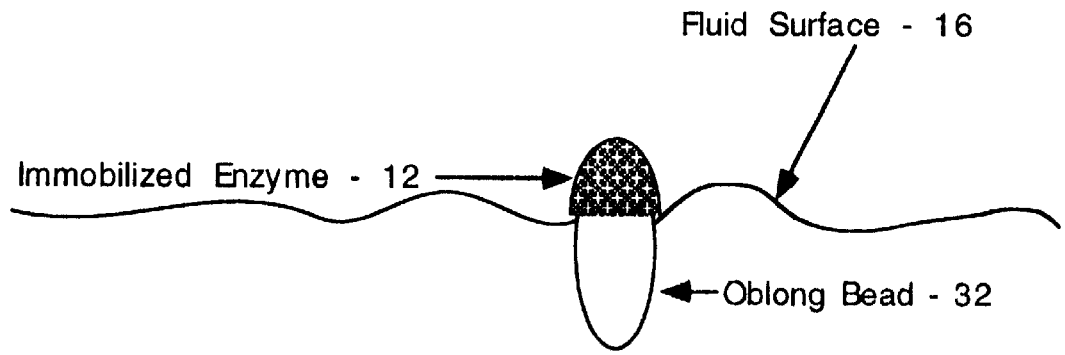
FIGS. 5a,5b illustrates buoyant beads for positioning enzyme at a liquid surface to facilitate transfer of a selected gas to a liquid phase.
Figure 5:
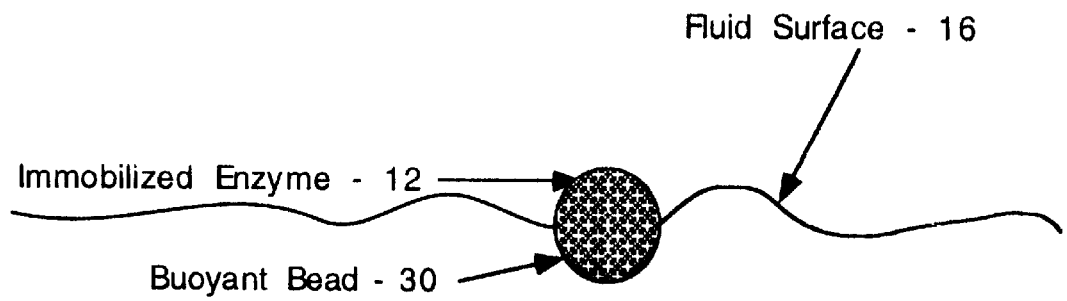
Figure 6:
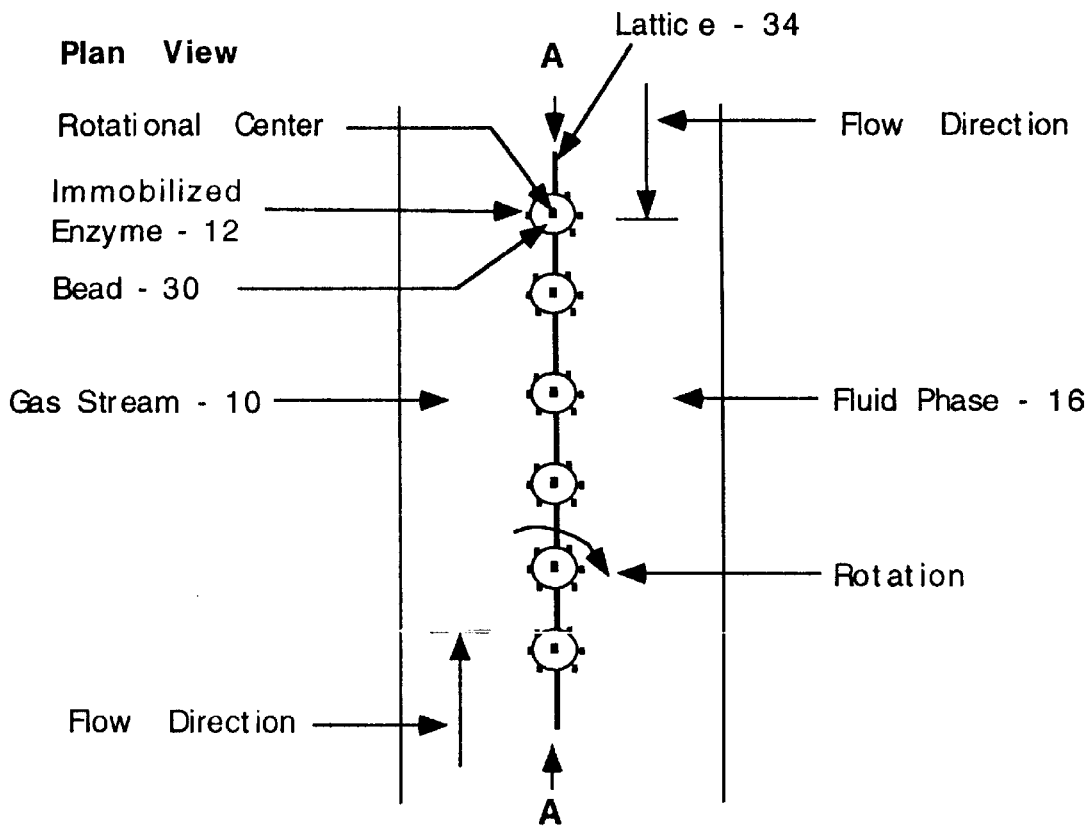
FIG. 6 Phase rotating immobilized enzyme carrier, plan view.
Figure 7:
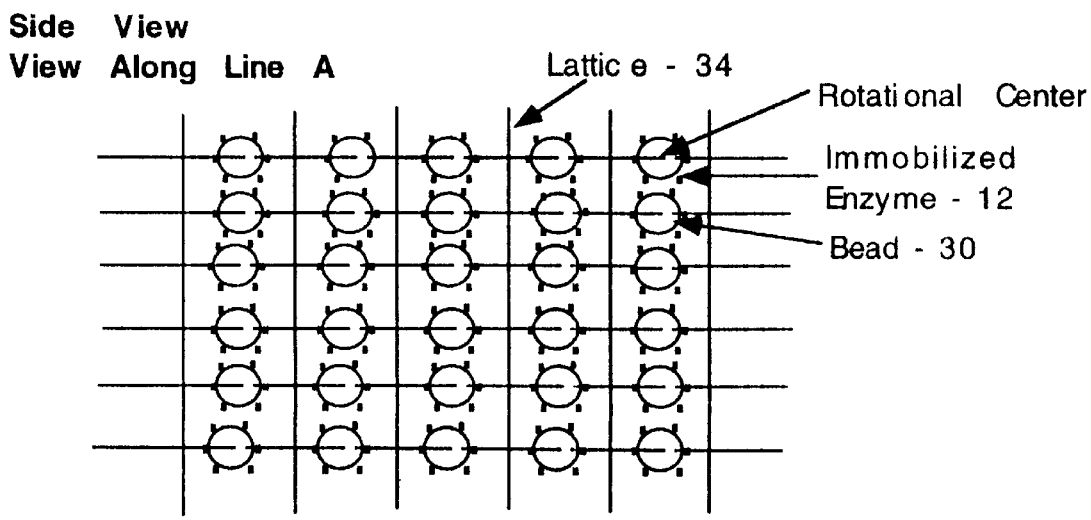
FIG. 7 Phase rotating immobilized enzyme carrier, side view.

The immobilization support 8 maybe of any conventional material such as polysaccharide surfaces or gels, ion exchange resin, treated silicon oxides, porus metal structures, carbon rods or tubes, graphite fibers, silica beads, cellulose membranes, gel matrices such as polyacrylamide gels, poly(acryloyl morpholine) gels, nylon or other polymer meshes, or other suitable binding surface. Alteratively the enzyme may be wholly or partially encapsulated in a suitable material such as cellulose nitrate capsules, polyvinyl alcohol capsules, starch capsules or liposome preparations. In another alternative the enzyme may be fixed at a phase boundary, as illustrated in FIGS. 5, 6 and 7 or by use of nonionic surfactants as described, for example in Li et al., U.S. Pat. No. 3,897,308.

The enzyme may be fixed to the surface by binding, covalent bonding, physical attraction, coordination bonds, chelation, or other binding means or mechanical trapping or other means known to those skilled in the art. The support may also be a membrane of selective permeability. The selectivity may be by size, or other characteristic. The membrane may be a lipid bilayer doped with passive porins, channels or ionophores of the co-porter or antiporter type which commonly rely on properties such as charge and/or hydrated radius for separation. Further examples of suitable materials for permeable portion 9 and support surface 8 include permeable membranes, natural and artificial, including semipermeable plastic membranes, black lipid membranes, alternatively doped with ionophores to provide ion conducting channels. In yet another embodiment the porins may be active, i.e., dependent on an energy flux. For example with a cell wall membrane, the energy flux may be tied to an endogenous high energy compound such as a labile triphosphate bond or to an exogenous supply of energy via photons, electrons or protons. In all these cases the immobilization support works as membrane with selective permeability to maintain separation of the mixed gas stream 10 from the second phase 16 while passing selected gas 14 into contact with second phase 16.

The enzymes immobilized on support surface 8 are of two types, simple enzymes and those requiring cofactors for activity. Simple enzymes may be fixed to the support surface by any of the means known to the art. Preferably the enzymes are modified by adding an amino acid sequence that binds to the support without substantially reducing enzyme activity. In a preferred embodiment the enzyme is modified by altering the DNA segment coding for the enzyme to add a sequence coding for an amino acid sequence that yields a binding moiety to the enzyme in a manner that enhances enzyme binding. The modification may provide a sequence that binds to a metal such as a polyhistidine sequence, or may code for an epitope or antigen moiety that binds to an antibody or may be a portion of an antibody that binds a known antigen. For example, a polyhistidine sequence can be added to an enzyme such as carbonic anhydrase by splicing a DNA fragment coding for the desired polyhistidine sequence into the DNA coding for the enzyme at either terminus of the protein sequence, and expressing the DNA in a suitable organism and recovering the new enzyme.

In the case of enzymes requiring cofactors the cofactor maybe supplied in second phase 16 or also fixed to the support surface 8 or supplied by pretreatment of surface 8 with the cofactor to activate bound enzyme. If multiple materials are to be bound to the support surface 8 they may be exposed to a prepared surface sequentially or as a mixture.

The second phase 16 may be selected from the group consisting of gases, aqueous solvents, protic solvents, aprotic solvents, hydrocarbon solvents, aromatic hydrocarbon solvents and supercritical fluids. The second phase may be stirred or a flow introduced by a pump to move fresh material into contact with the immobilized enzyme at the support surface. A flow may be introduced into second phase 16 by a stirrer or pump or other conventional means. Flow or other means is applied to maintain a concentration or other gradient to produce vectorial movement of the selected gas 14 into condensed phase 16. In some embodiments immobilization support 8 and film 26 maybe combined as, for example, in a lipid bilayer wherein a portion of the enzyme extends into the lipid bilayer to provide both support and an evaporation barrier.

In a preferred embodiment a film 26 is provided in which the selected gas is soluble, and which decreases the escape of second phase 16 into mixed gas stream 10. The film maybe a gel, hydrocarbon layer, or preferably a lipid or phospholipid layer or bilayer.

When the recovery zone 22 is used, the condensed phase 16 is contacted by a second surface which may carry a catalyst, enzyme or simply be selectively permeable such that selected gas 14 or its equivalent or derivative is transported to recovery zone 22. Again a concentration or other gradient may be used to enhance vectorial movement from second phase 16 into recovery phase 22.

Gases are defined as materials which are in the gas phase at ambient temperature and pressure (taken to be 20 degrees C. and one atmosphere). Suitable gases include nitrogen, oxygen, oxides of carbon, nitrogen, sulfur, methane, ammonia, hydrogen sulfide and the like. Any gas that interacts with an enzyme directly from the gas phase may be a selected gas 14 in combination with a suitable enzyme 12 which interacts with the selected gas 14. An enzyme is a protein or peptide that selectively binds or reacts with a gas molecule. An enzyme is composed of amino acids with an active site which binds a specific molecule and facilities a change in the bound molecule. An enzyme may include nonnaturally occurring amino acids, and maybe natural or artificial. Examples of suitable enzymes include:

| ENZYME | EC NUMBER |
|---|---|
| glucose oxidase | 1.1.3.4 |
| aldehyde oxidase | 1.2.3.1 |
| hydroxylamine oxidase | 1.7.3.4 |
| sulfite oxidase | 1.8.3.1 |
| sulfur-ferric ion oxidoreductase | 1.8.99.- |
| catechol oxidase (dimerizing) | 1.1.3.14 |
| laccase | 1.10.3.2 |
| L-ascorbate oxidase | 1.10.3.3 |
| catalase | 1.11.1.6 |
| sulfur dioxygenase | 1.13.11.18 |
| superoxide dismutase | 1.15.1.1 |
| B galactosidase | 3.2.1.23 |
| urease | 3.5.1.5 |
| carbonate dehydratase (carbonic anhydrase) | 4.2.1.1 |
| lactic acid oxygenase | |
| inositol oxygenase | |
| lysine oxygenase | |
| octane oxygenase | |
| pyrocatechase | |
| 3-hydroxyanthranilate oxygenase | |
| tryptophan oxygenase | |
| homogentisate oxygenase | |

CLASS II-GAS ENZYMES REQUIRING COFACTORS OR COENZYMES

| ENZYME | E NUMBBR | COFACTOR/COENZYME |
|---|---|---|
| formate dehydrogenase | 1.2.1.2 | NADH |
| formate dehydrogenase (cytochrome) | 1.2.2.1 | ferricytochrome $b_1$ |
| carbon monoxide-methylene blue oxidoreductase | 1.2.3.- | methylene blue |
| carbon monoxide dehydrogenase | 1.2.99.2 | methyl viologen |
| nitrate reductase (NADH) | 1.6.6.1 | NADH |
| nitrate reductase (NAD(P)H) | 1.6.6.2 | NAD(P)H |
| nitrate reductase (NADPH) | 1.6.6.3 | NADPH |
| nitrate reductase NAD(P)H | 1.6.6.4 | NAD(P)H |
| superoxide-forming enzyme | 1.6.99.- | NADPH |
| nitrite reductase (cytochrome) | 1.7.2.1 | ferricytochrome c |
| ferredoxin-nitrate | 1.7.7.1 | ferredoxin |
| hydroxylamine reductase | 1.7.99.1 | pyocyanine; methylene blue flavins |
| nitric-oxide reductase | 1.7.99.2 | pyocyanine |
| nitrite reductase | 1.7.99.3 | pyocyanine; flavins |
| nitrite reductase | 1.7.99.4 | benzyl viologen |
| sulfite reductase (NADPH) | 1.8.1.2 | NADP |
| sulfite reductase (ferredoxin) | 1.8.7.1 | ferredoxin |
| sulfite reductase | 1.8.99.1 | methyl viologen |
| adenyl sulfate reductase | 1.8.99.2 | methyl viologen |
| cytochrome c oxidase | 1.9.3.1 | ferrocytochrome |
| Pseudomonas cytochrome c oxidase | 1.9.3.2 | ferrocytochrome |
| nitrate reductase | 1.9.6.1 | ferrocytochrome |
| methane monoxygenase | 1.14.13.25 | NAD(P)H |
| nitrogenase | 1.18.2.1 | ferredoxin + ATP |
| carbamoyl-phosphate synthetase | 6.3.4.16 | ATP |

One skilled in the are will add other enzymes as need to satisfy the intent of this invention. As used herein the term enzyme should be taken to mean the enzyme per se, its cofactors and co-enzymes, i.e., all of the elements needed for a functional enzyme system to effect biochemical transformations.

EXAMPLE 1

To immobilize the enzyme on a membrane or mesh surface, such as, for example, nylon, one proceeds as follows: The material is activated by exposure to a 0.2 M nitric acid wash. The activated surface is exposed to 2 M sodium carbonate solution containing 20 g of disodium iminodiacetic acid (IDA) for 24 h at 60–65 C. The material is then rinsed with 0.1 M sodium carbonate, 0.01 M sodium acetate and water. It is then charged using zinc chloride at 1 mg/ml. Additional immobilized metal affinity chromatography (IMAC) procedures are found in Smith M C, Furman T C, Ingolia T D, and Pidgeon C (1988) Chelating Peptide-immobilized Metal Ion Affinity Chromatography: a new concept in affinity chromatography for recombinant proteins. *J. Biol. Chem.* 263:7211–7215., and Sulkowski E (1987) Immobilized metal ion affinity chromatography of proteins. In: Burgess R (ed.) *Protein Purification. Micro to Macro.* Alan R. Liss, Inc. New York pp. 149–162. The basis of protein retention is binding of amino acids on the protein surface (notably histidine) to the vacant coordination sites of metals (e.g., copper, zinc) complexed to chelating groups such as N-(carboxymethyl) glycine. The IDA ligand is favored because it is resistant to Ph between 2 and 13, and temperatures to at least 120 C.

EXAMPLE 2

In a reactor as illustrated by FIG. 2, a carbonic anhydrase (CA) (E 4.2.1.1) is immobilized on both sides of a reservoir of aqueous buffer. As noted above CA is the one of the fastest enzymes known with a turnover number of 600,000 katals. Thus it has the ability to catalyze the hydration of 600,000 molecules of carbon dioxide per second per molecule of CA. Carbonic anhydrase is a diffusion limited enzyme. Thus, any $CO_2$ molecule which comes into contact with the enzyme will be converted virtually immediately into $HCO_3^-$.

Any carbon dioxide containing mixed gas supply might be used. The scale of the equipment to be used must be adjusted accordingly. In this example, the mixed gas supply is taken from the exhaust stack of a gas fired electric power plant following appropriate heat exchangers and after passage of the exhaust through an air house. The make up of a typical gas is $N_2$—64.92%, $O_2$—2.04%, $CO_2$—7.06%, and $H_2O$—25.98%.

Any heavy metals which could foul the enzyme are first extracted from the mixed gas supply 10. Such metals could be present in the exhaust of a coal fired furnace. CA contains a zinc atom and other divalent cations can, under correct circumstances, displace the zinc and alter the reactivity of the enzyme. Cobalt is a particularly potent divalent cation of this class.

The enzyme is covered with a thin oil film 26 to prevent water loss from the second phase 16. I this example the second phase is an aqueous 20 mM sodium phosphate buffer. CA catalyzes the hydration of $CO_2$ to $HCO_3^-$. The bicarbonate is delivered to the flowing buffer stream of the second phase 16 and carried to contact the permeable wall area adjacent recovery one 22 where it contacts a second layer of CA fixed to support surface 8 at permeable wall area 9. The CA layer reverses the reaction and converts $HCO_3^-$ to $CO_2$. The second phase 16 buffer stream is constantly flowing to deliver lean buffered medium to the bicarbonate rich zone adjacent to the mixed gas supply 10 and then carry the bicarbonate rich fluid to the surface adjacent the recovery zone 22. The flow removes bicarbonate from the first surface where it can act as a competitive inhibitor of CA and slow the reaction. The overall effect is to create a continuous removal of product adjacent the enzyme surfaces and maintain a gradient that favors vectorial movement of $CO_2$ into solution as bicarbonate adjacent mixed gas stream 10 and from bicarbonate to $CO_2$ adjacent zone 22.

Carbonic anhydrase has a dehydrating rate constant which is slightly slower than the hydrating rate constant. For equal molar volumes of carbon dioxide and bicarbonate this favors the hydration of carbon dioxide. However, adjusting the relative surface area of the two enzyme surfaces will compensate for this difference. The newly generated $CO_2$ is drawn into recovery zone 22 at low pressure for extraction. This guarantees a vectorial flow for the entire system.

The kinetics and the specificity of the enzyme greatly favor the removal of $CO_2$ from the mixed gas supply above all other gases. Carbonic anhydrase does not recognize or interact with any of the other gases in the flue gas mixture. However, under steady state conditions the concentration and solubility of the several gases in the mixed gas stream will determine the degree to which they may pollute the purified gas stream. The solubility of these gases in oil and in water at 37 ÛC is given in Table I. The permeability of $CO_2$ in water is $210*10^{-9}*cm^3$ (STP)$*cm/sec*cm^2*cm$-Hg. The diffusivity of $CO_2$ in water is $1.96*10^{-5}*cm^2/sec$. The solubility of $CO_2$ in water is $3.39*10^{-5}$ gmoles$*cm*10^{-3}$/atm.

TABLE I

| GAS | OIL ml gas/ml oil | RATIO to $CO_2$ | WATER ml gas/ml water | Ratio to $CO_2$ |
|---|---|---|---|---|
| Nitrogen | 0.067 | 0.037:1 | 0.014 | 0.023:1 |
| Oxygen | 0.13 | 0.099:1 | 0.027 | 0.043:1 |
| Carbon dioxide | 1.34 | 1:1 | 0.63 | 1:1 |
| Carbon monoxide | 0.097 | 0.073:1 | 0.012 | 0.034:1 |
| Methane | 0.31 | 0.231:1 | 0.029 | 0.046:1 |

Given the solubility ratio, vis-a-vis $CO_2$ dissolving into the system and the respective concentrations the expected contamination of purified gas stream by each gas in the exhaust stream of the electric power plant in a single pass is: $N_2$—0.9%, $O_2$—0.006%, $H_2O$—0%, CO—0%, $CH_4$—0%. The buffer and other salts do not appreciably alter the gas solubility and the rate of dissolution of carbon dioxide in water is $10^7$ times slower in the absence of carbonic anhydrase. In the absence of enzymatic conversion over 99% of the $CO_2$ remains in the dissolved gas form and less than 1% is spontaneously converted to bicarbonate, and very little gas would be recovered in recovery zone 22.

EXAMPLE 3

In FIG. 3 a two stage reactor of the same general design and operation as that illustrated in Example 2 is shown. The inlet mixed gas 10 is preferably a carbon dioxide rich stream. On the mixed gas stream side carbonic anhydrase is the immobilized enzyme 12 which is covered by a lipid film 26 as in Example 2. Carbon dioxide is converted to bicarbonate adjacent the mixed gas side also as described in Example 2. A separate supply line 28 injects ammonia into the aqueous phase 16, which is converted to ammonium carbonate by conventional chemical reaction with the bicarbonate. The ammonium carbonate rich aqueous phase is circulated to contact urease 12 immobilized on a semipermeable membrane 9 adjacent urea recovery zone 22. The ammonium carbonate from the aqueous buffer is converted to urea by urease and transported across the membrane to the recovery zone via absorption. An organic solvent in the recovery zone dissolves the urea which is conveyed away from permeable zone 9, for recovery. The urea stream is flash evaporated to concentrate the urea while the solvent is returned to zone 22 and recycled.

EXAMPLE 4

Figure 4:
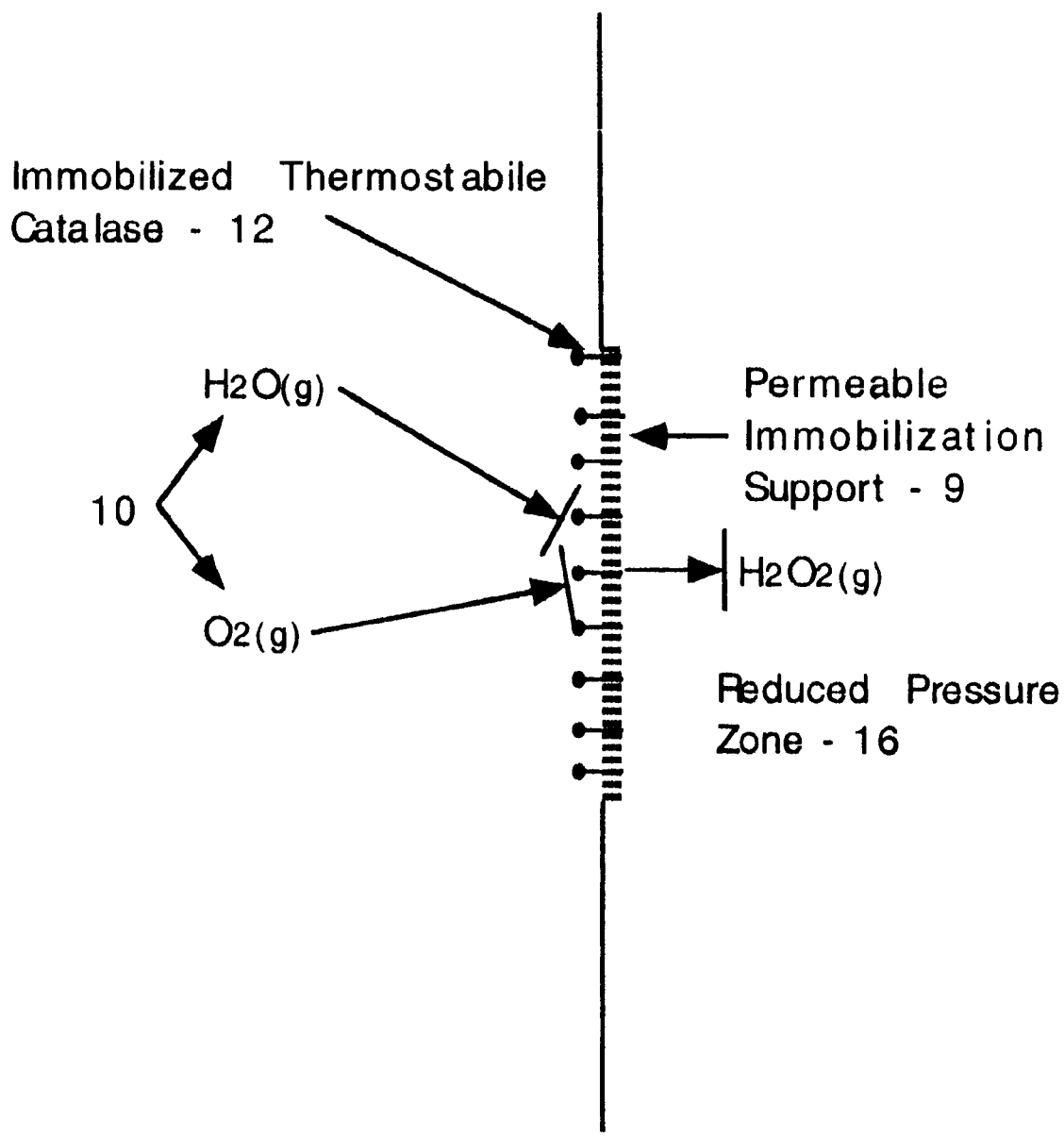
FIG. 4 shows a reactor for conversion of oxygen and water to hydrogen peroxide.

The operation of a gas phase to gas phase bioreactor is illustrated in FIG. 4. The immobilized enzyme 12 is catalase and the selected gas from mixed gas stream 10 is oxygen. Catalase normally catalyzes the reaction $H_2O_2 ==> \frac{1}{2} O_2 + H_2O$. Catalase is a diffusion limited or "perfect enzyme". Its reaction rate is about $5.6*10^6$ mol/mol/min. $\Delta G$ for the reaction of hydrogen peroxide to produce oxygen and water in the uncatalyzed state is 18 kcal/mol. When catalyzed by a typical physical catalyst, platinum, this value drops to 13 kcal/mol, an improvement of only 38%. However, when catalyzed by catalase it declines dramatically to 7 kcal/mol, an improvement over platinum of 86% and a total improvement of 257%. This reaction is exothalmic in the amount of 45.68 kcal/gmol in aqueous phase and 25.97 kcal/gmol in gas phase.

The reaction can be forced to proceed in the opposite direction, using $O_2$ and $H_2O$ vapor to produce $H_2O_2$. If the raw materials $O_2$ and $H_2O$ vapor are supplied at elevated temperature, or other means, sufficient to overcome the energy barrier, then $H_2O_2$ can be generated. It is important to maintain this reaction in the gas phase first to minimize the energy differences and second to prevent the deleterious effect of even moderate concentrations of peroxide on the integrity of the enzyme. It is also important that the second side is at lower pressure than the first side to provide vectorial flow to the system and remove the peroxide from the enzyme before an appreciable concentration accumulates. Due to its specificity catalase is unreactive to other gases commonly found in air, for example. Water vapor is supplied to the enzyme by increasing the humidity of the mixed gas stream 10, preferably to near 100%. Water vapor at near 100% humidity provides sufficient water to hydrate the active site of the enzyme. The consequence of the exemplified operation is the production of enriched peroxide in the second phase 16.

EXAMPLE 5

A simplified bioreactor is illustrated in FIG. 5 wherein an enzyme 12 such as carbonic anhydrase is coated on the surface of a buoyant bead 30 which floats at the surface of a fluid. A gas stream contacts the exposed enzyme on the exposed surface of the floating bead, and the enzyme binds its gas substrate. Turbulence of the fluid at the surface rotates the bead to immerse enzyme with bound substrate and wash away the product of the enzymatic reaction into the fluid phase. In the case of carbonic anhydrase, carbon dioxide in a mixed gas such as the atmosphere is bound and converted to bicarbonate. Rotation of the bead immerses enzyme carrying bound carbon dioxide or bicarbonate and exposes fresh enzyme to the atmosphere. When the beads float on a water surface, the net effect is to facilitate the conversion of carbon dioxide in the mixed gas to bicarbonate in aqueous solution. Such a bead reactor may be incorporated for example into a conventional scrubber to reduce the amount of carbon dioxide released into the atmosphere by a fossil fuel fired power generation plant. Beads floating on the surface of a pond may be useful to remove carbon dioxide from the atmosphere and increase the available bicarbonate concentration in the water. Also shown in FIG. 5 are oblong beads 32 which may be partially coated with enzyme and weighted to maintain the enzyme exposed to the gas phase. An alternate embodiment uses fully coated beads 30 of a selected density to float at the fluid surface with a portion of the enzyme directly exposed to the gas phase. While any fluid may be employed provided that the enzyme remains active and product is washed off into the fluid phase, water or aqueous buffers are the preferred fluids.

An alternative embodiment uses a structure similar to that shown in FIG. 6. Beads having enzyme immobilized on the surface are fixed to a lattice 34 in such a manner that the beads can rotate around a lattice element. The lattice 34 is positioned such that the beads are fixed at the surface of a fluid phase in contact with a gas stream. The gas stream impinges on the beads such that the force of the gas stream 10 is sufficient to rotate the beads exposing fresh enzyme surface to the gas and carrying bound gas into contact with the fluid phase 16. The turbulence is such that the bead 30 carrying the immobilized enzyme rotates to be successively exposed to the gas phase and the fluid phase 16.

EXAMPLE 6

The bioreactor illustrated in FIGS. 6 and 7 utilizes countercurrent flow of the two phases on opposite sides of the immobilized enzyme affixed to axially tethered bead-like immobilization surfaces. Under these circumstances the beads will rotate moving the surface from contacting the first fluid to contacting the second fluid and vice versa. Gases or products will be delivered from the first fluid to the second fluid where they will be deposited. The effect of the immobilized enzyme at the bead surface is to facilitate transfer of a gas or product from the first fluid to the second fluid. Preferably the countercurrent fluids are immiscible or are separated by a semipermeable layer which may partially overlay the bead support lattice 34 to separate the countercurrent fluids. The beads are sized to extend beyond the separating layer and contact each fluid. In another embodiment the beads of FIGS. 6 or 7 may includes vanes to facilitate rotation by the fluid flow. Disks or other shaped supports may be substituted for spherical beads in this embodiment.

In the bioreactors of Examples 5 and 6, material choices for beads, immobilization methods, solvents, buffers and enzymes are the same as those discussed above for the other systems. In the floating bead reactor of Examples 5 and 6 much of the structure is eliminated while the essential features of the invention are retained.

In each of the preceding examples, the choice of fluid, buffer and salt content is determined by both the solubility and ionization potential of ionic equivalents of the gas of interest in the fluid, on both an absolute scale and in relation to the solubility and formation of ionic equivalents of other gases in the mixed gas stream. The following factors guide the choice. One is to increase the fractional concentration of the gas of interest. Another is to decrease the fractional concentration of contaminants. Yet another is to increase the ability of chemical reactions to occur in the medium and to increase the ability of the enzyme to generate ionic equivalents. Another is to optimize the miscibility of the gas with the phase surrounding the enzyme.

Many variations of structure and design may be made to combine the elements of the disclosed invention in many configuration without departing from the scope and spirit of the present invention as defined by the appended claims.

I claim:

1. A bioreactor which comprises a vessel having at least one first wall enclosing an inlet zone, and at least one second wall enclosing a second phase zone, a portion of the second wall is permeable to at least one selected gas in the inlet zone, and retains the second phase in the second phase zone; a portion of the second wall also comprises a support surface with at least one enzyme fixed thereon, such that a mixed gas stream entering the inlet zone contacts enzyme which removes a selected gas from the mixed gas stream and passes the selected gas to the second phase zone.

2. A bioreactor according to claim 1 which further comprises a recovery zone enclosed by a second wall which comprises a selectively permeable area which retains the second phase while passing a selected product obtained by action of enzyme on a selected gas from the mixed gas stream.

3. A bioreactor according to claim 2 wherein a catalyst is fixed to the selectively permeable area between the second phase and the recovery zone such that a chemical change results when a substance in the second phase contacts the catalyst, and the product of the chemical change enters the recovery zone.

4. A bioreactor according to claim 3 wherein the catalyst is an enzyme.

5. A bioreactor according to claim 4 wherein the selected gas removed from the mixed gas stream is recovered in the recovery zone.

6. A bioreactor according to claim 5 wherein the selected gas is carbon dioxide.

7. A bioreactor according to claim 1 wherein the enzyme is carbonic anhydrase.

* * * * *